(12) United States Patent
Hourmand et al.

(10) Patent No.: US 12,076,541 B2
(45) Date of Patent: Sep. 3, 2024

(54) AUTOINJECTOR WITH AN INNER PLUNGER WHICH DISENGAGES THE OUTER PLUNGER TO RETRACT THE SYRINGE CARRIER

(71) Applicant: SANOFI-AVENTIS DEUTSCHLAND GMBH, Frankfurt am Main (DE)

(72) Inventors: Yannick Hourmand, Haslingfield Cambridge (GB); Simon Brereton, Cambridgeshire (GB); Thomas Mark Kemp, Ashwell (GB); Rosie Burnell, Cambridge (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 547 days.

(21) Appl. No.: 16/848,524

(22) Filed: Apr. 14, 2020

(65) Prior Publication Data
US 2020/0261661 A1 Aug. 20, 2020

Related U.S. Application Data

(63) Continuation of application No. 15/821,166, filed on Nov. 22, 2017, now Pat. No. 10,653,851, which is a
(Continued)

(30) Foreign Application Priority Data

Dec. 21, 2011 (EP) .................. 11194775

(51) Int. Cl.
*A61M 5/32* (2006.01)
*A61M 5/20* (2006.01)

(52) U.S. Cl.
CPC .......... *A61M 5/326* (2013.01); *A61M 5/2033* (2013.01); *A61M 2005/2013* (2013.01); *A61M 2005/206* (2013.01)

(58) Field of Classification Search
CPC .......... A61M 5/2033; A61M 2005/206; A61M 5/326; A61M 5/3202
(Continued)

(56) References Cited

U.S. PATENT DOCUMENTS

| 4,964,866 A | 10/1990 | Szwarc |
| 5,478,316 A | 12/1995 | Bitdinger et al. |

(Continued)

FOREIGN PATENT DOCUMENTS

| CN | 101678167 | 3/2008 |
| DE | 19819409 | 11/1999 |

(Continued)

OTHER PUBLICATIONS

International Preliminary Report on Patentability in International Application No. PCT/EP2012/076097, dated Jun. 24, 2014, 8 pages.
(Continued)

*Primary Examiner* — Phillip A Gray
(74) *Attorney, Agent, or Firm* — Fish & Richardson P.C.

(57) ABSTRACT

Described is an autoinjector comprising a case, a chassis slidably arranged in the case, a syringe carrier operably coupled to the chassis, an outer plunger selectively engaged to the chassis, an inner plunger selectively engaged to the outer plunger, and a drive spring applying a biasing force to the outer plunger. The biasing force is applied to the inner plunger when the inner plunger is engaged to the outer plunger. Rotation of the chassis causes the inner plunger to rotate relative to the outer plunger and disengage the outer plunger to remove the biasing force from the drive spring on the inner plunger. When the inner plunger disengages the outer plunger, the biasing force of the drive spring pushes the chassis to retract the syringe carrier relative to the case.

23 Claims, 9 Drawing Sheets

Related U.S. Application Data continuation of application No. 14/366,868, filed as application No. PCT/EP2012/076097 on Dec. 19, 2012, now Pat. No. 9,827,381.

(58) Field of Classification Search
USPC .................................................. 604/198
See application file for complete search history.

(56) References Cited

U.S. PATENT DOCUMENTS

| | | |
|---|---|---|
| 5,480,387 A | 1/1996 | Gabriel et al. |
| 5,559,309 A | 9/1996 | Zabler et al. |
| 5,599,309 A | 2/1997 | Marshall et al. |
| 6,004,297 A | 12/1999 | Steenfeldt-Jensen et al. |
| 6,277,099 B1 | 8/2001 | Strowe et al. |
| 6,371,939 B2 | 4/2002 | Bergens et al. |
| 6,454,743 B1 | 9/2002 | Weber |
| 6,620,137 B2 | 9/2003 | Kirchhofer et al. |
| 6,743,205 B2 | 6/2004 | Nolan, Jr. et al. |
| 7,195,616 B2 | 3/2007 | Diller et al. |
| 7,291,132 B2 | 11/2007 | DeRuntz et al. |
| 7,297,135 B2 | 11/2007 | Jeffrey |
| 7,341,575 B2 | 3/2008 | Rice et al. |
| 7,597,685 B2 | 10/2009 | Olson |
| 7,678,085 B2 | 3/2010 | Graf |
| 7,717,877 B2 | 5/2010 | Lavi et al. |
| 7,771,398 B2 | 8/2010 | Knight et al. |
| 7,976,494 B2 | 7/2011 | Kohlbrenner et al. |
| 8,038,649 B2 | 10/2011 | Kronestedt |
| 8,048,037 B2 | 11/2011 | Kohlbrenner et al. |
| 8,062,255 B2 | 11/2011 | Brunnberg et al. |
| 8,083,711 B2 | 12/2011 | Enggaard |
| 8,313,465 B2 | 11/2012 | Harrison |
| 8,323,238 B2 | 12/2012 | Cronenberg et al. |
| 8,357,125 B2 | 1/2013 | Grunhut et al. |
| 8,361,025 B2 | 1/2013 | Lawlis et al. |
| 8,366,680 B2 | 2/2013 | Raab |
| 8,376,993 B2 | 2/2013 | Cox et al. |
| 8,376,997 B2 | 2/2013 | Hogdahl et al. |
| 8,403,883 B2 | 3/2013 | Fayyaz et al. |
| 8,409,141 B2 | 4/2013 | Johansen et al. |
| 8,409,148 B2 | 4/2013 | Fiechter et al. |
| 8,439,864 B2 | 5/2013 | Galbraith et al. |
| 8,491,538 B2 | 7/2013 | Kohlbrenner et al. |
| 8,568,359 B2 | 10/2013 | Carrel et al. |
| 8,617,109 B2 | 12/2013 | Kronestedt et al. |
| 8,617,124 B2 | 12/2013 | Wieselblad et al. |
| 8,632,507 B2 | 1/2014 | Bartha |
| 8,647,299 B2 | 2/2014 | Stamp |
| 8,684,969 B2 | 4/2014 | Moller et al. |
| 8,708,973 B2 | 4/2014 | Holmqvist |
| 8,734,402 B2 | 5/2014 | Sharp et al. |
| 8,758,292 B2 | 6/2014 | Tschirren et al. |
| 8,808,250 B2 | 8/2014 | Ekman et al. |
| 8,808,251 B2 | 8/2014 | Raab et al. |
| 8,821,451 B2 | 9/2014 | Daniel |
| 8,834,431 B2 | 9/2014 | Kohlbrenner et al. |
| 8,840,591 B2 | 9/2014 | Raab et al. |
| 8,882,723 B2 | 11/2014 | Smith et al. |
| 8,911,411 B2 | 12/2014 | Nielsen |
| 8,939,934 B2 | 1/2015 | Brereton et al. |
| 8,945,063 B2 | 2/2015 | Wotton et al. |
| 8,956,331 B2 | 2/2015 | Johansen et al. |
| 8,961,473 B2 | 2/2015 | Heald |
| 8,968,256 B2 | 3/2015 | Raab |
| 8,968,258 B2 | 3/2015 | Nzike et al. |
| 8,992,484 B2 | 3/2015 | Radmer et al. |
| 8,992,487 B2 | 3/2015 | Eich et al. |
| 9,005,160 B2 | 4/2015 | Karlsson et al. |
| 9,011,386 B2 | 4/2015 | Kronestedt et al. |
| 9,011,387 B2 | 4/2015 | Ekman et al. |
| 9,022,982 B2 | 5/2015 | Karlsson et al. |
| 9,022,991 B1 | 5/2015 | Moeller |
| 9,022,993 B2 | 5/2015 | Dasbach et al. |
| 9,022,994 B2 | 5/2015 | Moser et al. |
| 9,044,548 B2 | 6/2015 | Miller et al. |
| 9,044,553 B2 | 6/2015 | James et al. |
| 9,057,369 B2 | 6/2015 | Kohlbrenner et al. |
| 9,061,104 B2 | 6/2015 | Daniel |
| 9,067,024 B2 | 6/2015 | Roberts et al. |
| 9,072,838 B2 | 7/2015 | Hogdahl |
| 9,089,652 B2 | 7/2015 | Nzike et al. |
| 9,108,002 B2 | 8/2015 | Markussen |
| 9,125,988 B2 | 9/2015 | Karlsson |
| 9,132,235 B2 | 9/2015 | Holmqvist |
| 9,132,236 B2 | 9/2015 | Karlsson et al. |
| 9,199,038 B2 | 12/2015 | Daniel |
| 9,205,199 B2 | 12/2015 | Kemp et al. |
| 9,233,214 B2 | 1/2016 | Kemp et al. |
| 9,233,215 B2 | 1/2016 | Hourmand et al. |
| 9,242,044 B2 | 1/2016 | Markussen |
| 9,272,098 B2 | 3/2016 | Hourmand et al. |
| 9,283,326 B2 | 3/2016 | Kemp et al. |
| 9,283,327 B2 | 3/2016 | Hourmand et al. |
| 9,283,328 B2 | 3/2016 | Dasbach |
| 9,308,327 B2 | 4/2016 | Marshall et al. |
| 9,333,304 B2 | 5/2016 | Brereton et al. |
| 9,339,607 B2 | 5/2016 | Langley et al. |
| 9,352,088 B2 | 5/2016 | Ekman et al. |
| 9,358,345 B2 | 6/2016 | Brereton et al. |
| 9,358,351 B2 | 6/2016 | Ekman et al. |
| 9,393,368 B2 | 7/2016 | Nzike et al. |
| 9,408,976 B2 | 8/2016 | Olson et al. |
| 9,408,977 B2 | 8/2016 | Butler et al. |
| 9,408,979 B2 | 8/2016 | Veasey et al. |
| 9,415,165 B2 | 8/2016 | Cowe |
| 9,421,336 B2 | 8/2016 | Ekman et al. |
| 9,427,525 B2 | 8/2016 | Barrow-Williams et al. |
| 9,427,527 B2 | 8/2016 | Dasbach et al. |
| 9,446,195 B2 | 9/2016 | Kramer et al. |
| 9,446,196 B2 | 9/2016 | Hourmand et al. |
| 9,446,201 B2 | 9/2016 | Holmqvist |
| 9,457,149 B2 | 10/2016 | Kemp et al. |
| 9,457,152 B2 | 10/2016 | Raab et al. |
| 9,492,622 B2 | 11/2016 | Brereton et al. |
| 9,662,452 B2 | 5/2017 | Daniel |
| 9,717,851 B2 | 8/2017 | Fabien et al. |
| 9,724,472 B2 | 8/2017 | Hourmand et al. |
| 9,867,940 B2 | 1/2018 | Holmqvist et al. |
| 9,895,492 B2 | 2/2018 | Fabien et al. |
| 10,420,898 B2 | 9/2019 | Daniel |
| 10,500,337 B2 | 12/2019 | Fabien et al. |
| RE47,903 E | 3/2020 | Hourmand et al. |
| 10,729,853 B2 | 8/2020 | Hourmand et al. |
| RE48,593 E | 6/2021 | Hourmand et al. |
| 11,400,217 B2 | 8/2022 | Hourmand et al. |
| 11,458,252 B2 | 10/2022 | Hourmand et al. |
| 11,471,601 B1 | 10/2022 | Hourmand et al. |
| 11,607,495 B1 | 3/2023 | Hourmand et al. |
| 11,612,691 B2 | 3/2023 | Hourmand et al. |
| 2002/0007154 A1 | 1/2002 | Hansen et al. |
| 2002/0095120 A1 | 7/2002 | Larsen et al. |
| 2003/0105430 A1 | 6/2003 | Lavi et al. |
| 2004/0039336 A1 | 2/2004 | Amark et al. |
| 2005/0101919 A1 | 5/2005 | Brunnberg |
| 2005/0222539 A1 | 10/2005 | Gonzales et al. |
| 2006/0153693 A1 | 7/2006 | Fiechter et al. |
| 2006/0224124 A1 | 10/2006 | Scherer |
| 2006/0258990 A1 | 11/2006 | Weber |
| 2006/0270985 A1 | 11/2006 | Hommann et al. |
| 2006/0287630 A1 | 12/2006 | Hommann |
| 2007/0027430 A1 | 2/2007 | Hommann |
| 2007/0129686 A1 | 6/2007 | Daily et al. |
| 2008/0262427 A1 | 10/2008 | Hommann |
| 2008/0262438 A1 | 10/2008 | Bollenbach et al. |
| 2008/0312591 A1 | 12/2008 | Harrison |
| 2009/0012471 A1 | 1/2009 | Harrison |
| 2009/0088688 A1 | 4/2009 | Barrow-Williams et al. |
| 2009/0292246 A1 | 11/2009 | Slate et al. |
| 2009/0312705 A1 | 12/2009 | Grunhut et al. |
| 2010/0049125 A1 | 2/2010 | James et al. |
| 2010/0152659 A1 | 6/2010 | Streit et al. |
| 2010/0185178 A1 | 7/2010 | Sharp et al. |
| 2010/0256570 A1 | 10/2010 | Maritan |

(56) References Cited

U.S. PATENT DOCUMENTS

| | | | |
|---|---|---|---|
| 2010/0262083 A1 | 10/2010 | Grunhut et al. | |
| 2010/0268170 A1 | 10/2010 | Carrel et al. | |
| 2010/0312195 A1 | 12/2010 | Johansen et al. | |
| 2011/0213315 A1* | 9/2011 | Sweeney | A61M 5/2448 604/228 |
| 2011/0270161 A1 | 11/2011 | Harrison et al. | |
| 2012/0010575 A1 | 1/2012 | Jones et al. | |
| 2012/0041387 A1 | 2/2012 | Bruggemann et al. | |
| 2012/0053528 A1 | 3/2012 | Bollenbach et al. | |
| 2012/0116319 A1 | 5/2012 | Grunhut | |
| 2012/0172817 A1 | 7/2012 | Bruggemann et al. | |
| 2013/0035647 A1 | 2/2013 | Veasey et al. | |
| 2013/0041328 A1 | 2/2013 | Daniel | |
| 2013/0123710 A1 | 5/2013 | Ekman et al. | |
| 2013/0131595 A1* | 5/2013 | Ekman | A61M 5/2033 604/117 |
| 2013/0261556 A1 | 10/2013 | Jones et al. | |
| 2013/0274662 A1 | 10/2013 | Hourmand et al. | |
| 2013/0274666 A1 | 10/2013 | Brereton et al. | |
| 2013/0274677 A1 | 10/2013 | Ekman et al. | |
| 2013/0281942 A1 | 10/2013 | Teucher et al. | |
| 2013/0289525 A1 | 10/2013 | Kemp et al. | |
| 2013/0310757 A1 | 11/2013 | Brereton et al. | |
| 2013/0317428 A1 | 11/2013 | Brereton et al. | |
| 2013/0324925 A1 | 12/2013 | Brereton et al. | |
| 2013/0345643 A1 | 12/2013 | Hourmand et al. | |
| 2014/0336590 A1 | 11/2014 | Hourmand et al. | |
| 2014/0343508 A1 | 11/2014 | Hourmand et al. | |
| 2015/0100029 A1 | 4/2015 | Cowe et al. | |
| 2015/0133872 A1 | 5/2015 | Smith et al. | |
| 2015/0273157 A1 | 10/2015 | Kohlbrenner et al. | |
| 2016/0051767 A1 | 2/2016 | Higgins et al. | |
| 2016/0058950 A1 | 3/2016 | Marsh et al. | |
| 2016/0067415 A1 | 3/2016 | Bayer et al. | |
| 2016/0067418 A1 | 3/2016 | Morris et al. | |
| 2016/0089498 A1 | 3/2016 | Daniel | |
| 2016/0144129 A1 | 5/2016 | Mosebach et al. | |
| 2016/0144133 A1 | 5/2016 | Kemp | |
| 2016/0151585 A1 | 6/2016 | Kemp | |
| 2017/0326298 A1 | 11/2017 | Hourmand et al. | |
| 2018/0064875 A1 | 3/2018 | Holmqvist | |
| 2020/0316298 A1 | 10/2020 | Hourmand et al. | |
| 2022/0211947 A1 | 7/2022 | Hourmand et al. | |
| 2022/0218906 A1 | 7/2022 | Hourmand et al. | |
| 2022/0313915 A1 | 10/2022 | Hourmand et al. | |
| 2023/0019806 A1 | 1/2023 | Hourmand et al. | |
| 2023/0086760 A1 | 3/2023 | Hourmand et al. | |

FOREIGN PATENT DOCUMENTS

| | | |
|---|---|---|
| DE | 202007000578 | 3/2007 |
| DE | 102005052502 | 5/2007 |
| DE | 102007013836 | 9/2008 |
| EP | 0516473 | 5/1992 |
| EP | 0666084 | 8/1995 |
| EP | 0824923 | 2/1998 |
| EP | 0991441 | 12/2003 |
| EP | 2399630 | 12/2011 |
| EP | 2399634 | 12/2011 |
| EP | 2438947 | 4/2012 |
| EP | 2468334 | 6/2012 |
| EP | 2468335 | 6/2012 |
| GB | 2438592 | 12/2007 |
| JP | 2001-521792 | 11/2001 |
| JP | 2002-528182 | 9/2002 |
| JP | 2008-521482 | 6/2008 |
| JP | 2008-229344 | 10/2008 |
| JP | 2010-520786 | 6/2010 |
| JP | 2010-540059 | 12/2010 |
| WO | WO 1999/022790 | 5/1999 |
| WO | WO 1999/022792 | 5/1999 |
| WO | WO 1999/053979 | 10/1999 |
| WO | WO 2000/024441 | 5/2000 |
| WO | WO 2002/047746 | 6/2002 |
| WO | WO 2003/062672 | 7/2003 |
| WO | WO 2005/097238 | 10/2005 |
| WO | WO 2005/115507 | 12/2005 |
| WO | WO 2006/057604 | 6/2006 |
| WO | WO 2007/083115 | 7/2007 |
| WO | WO 2007/099044 | 9/2007 |
| WO | WO 2007/129324 | 11/2007 |
| WO | WO 2008/059385 | 5/2008 |
| WO | WO 2008/112472 | 9/2008 |
| WO | WO 2008/113864 | 9/2008 |
| WO | WO 2008/116688 | 10/2008 |
| WO | WO 2009/040602 | 4/2009 |
| WO | WO 2009/040607 | 4/2009 |
| WO | WO 2009/040672 | 4/2009 |
| WO | WO 2009/062508 | 5/2009 |
| WO | WO 2010/035060 | 4/2010 |
| WO | WO 2010/063707 | 6/2010 |
| WO | WO 2011/012903 | 2/2011 |
| WO | WO 2011/101375 | 8/2011 |
| WO | WO 2011/101379 | 8/2011 |
| WO | WO 2011/101383 | 8/2011 |
| WO | WO 2011/109205 | 9/2011 |
| WO | WO 2011/111006 | 9/2011 |
| WO | WO 2011/117592 | 9/2011 |
| WO | WO 2011/126439 | 10/2011 |
| WO | WO 2012/045350 | 4/2012 |
| WO | WO 2012/085021 | 6/2012 |
| WO | WO 2012/085024 | 6/2012 |
| WO | WO 2013/092670 | 6/2013 |
| WO | WO 2021/008839 | 1/2021 |

OTHER PUBLICATIONS

International Search Report in International Application No. PCT/EP2012/076097, dated Apr. 17, 2013.

Written Opinion in International Application No. PCT/EP2012/076097, dated Apr. 17, 2013.

International Preliminary Report on Patentability in International Appln. No. PCT/EP2011/073502, dated Jun. 25, 2013, 7 pages.

International Search Report and Written Opinion in International Appln. No. PCT/EP2011/073502, dated Mar. 19, 2012, 9 pages.

* cited by examiner

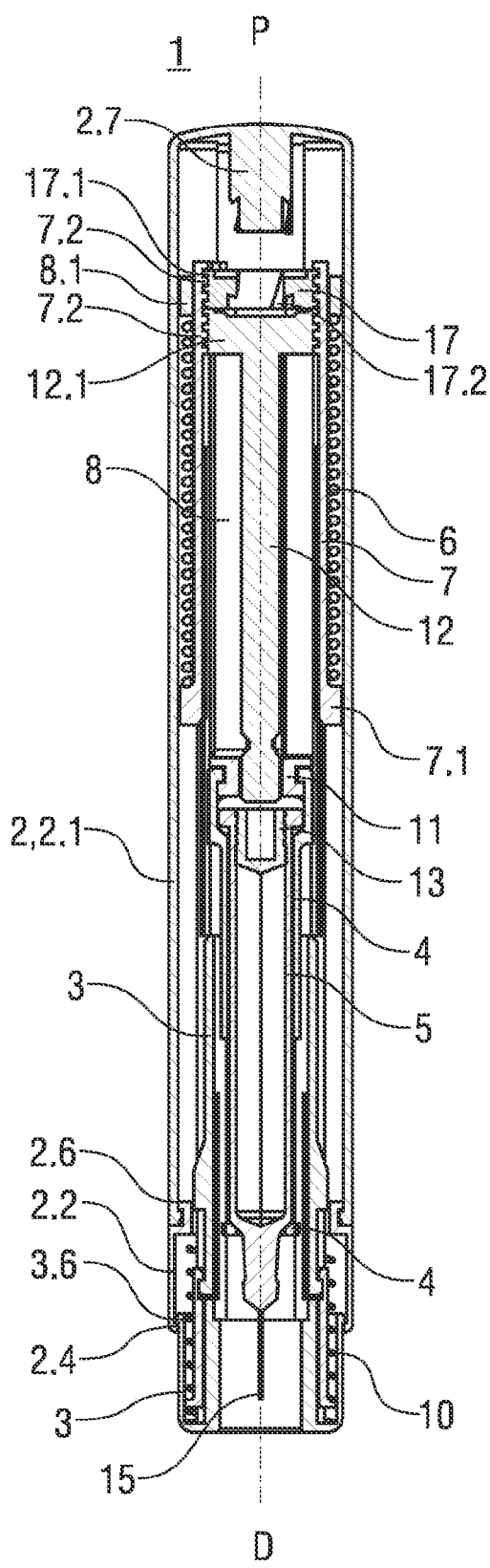
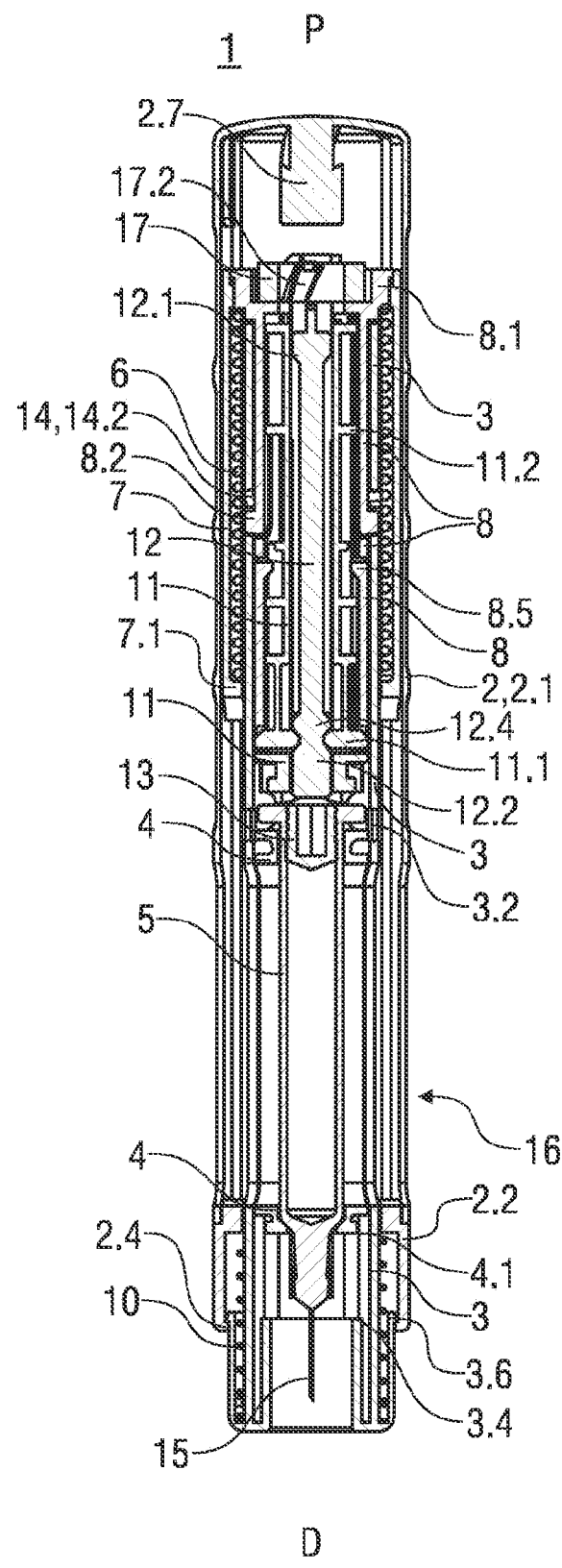
FIG 1A
FIG 1B

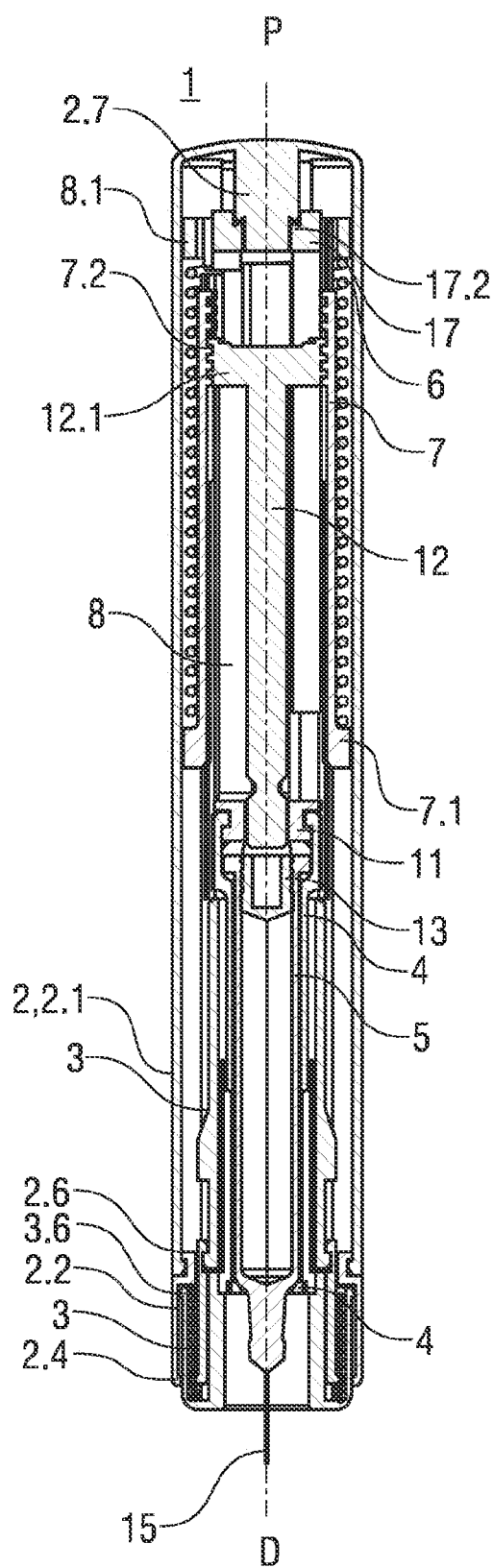
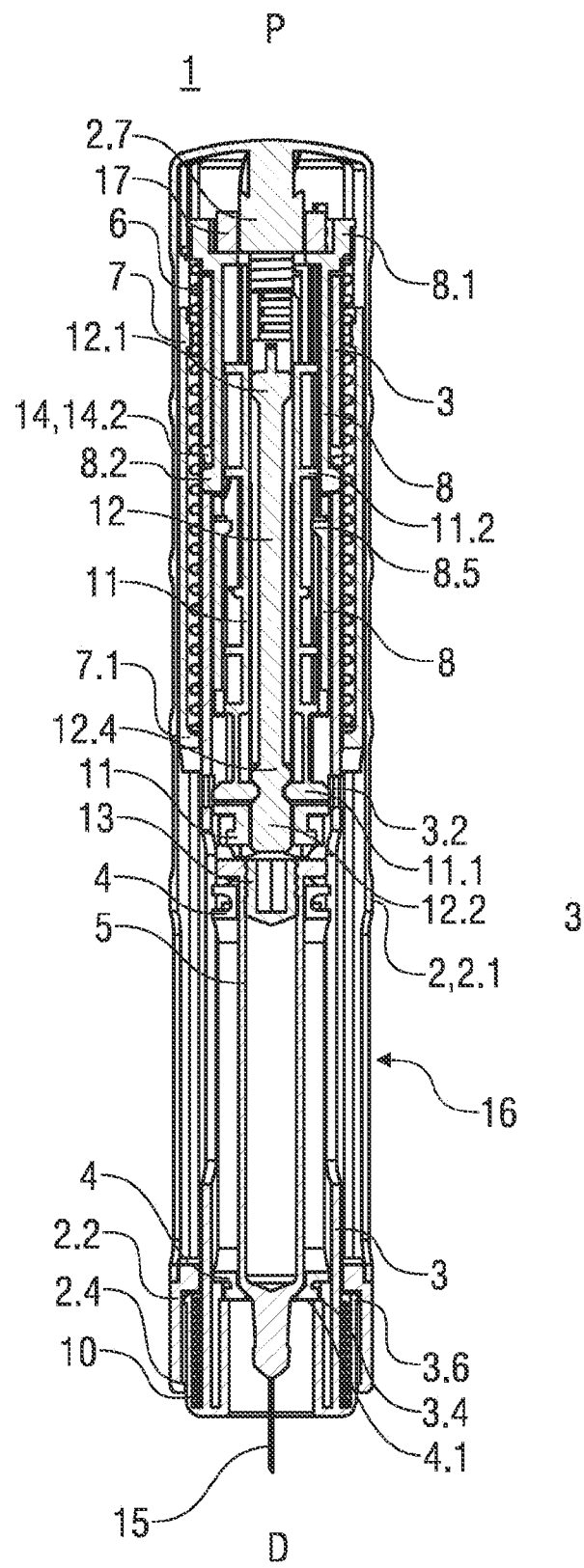
FIG 6A
FIG 6B

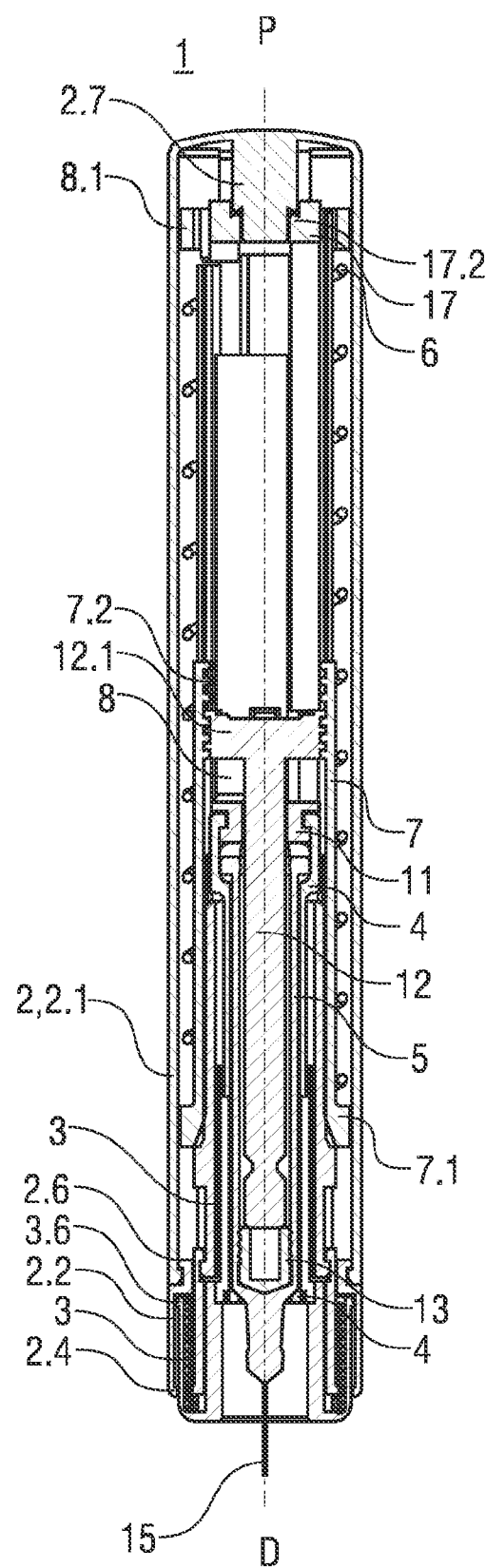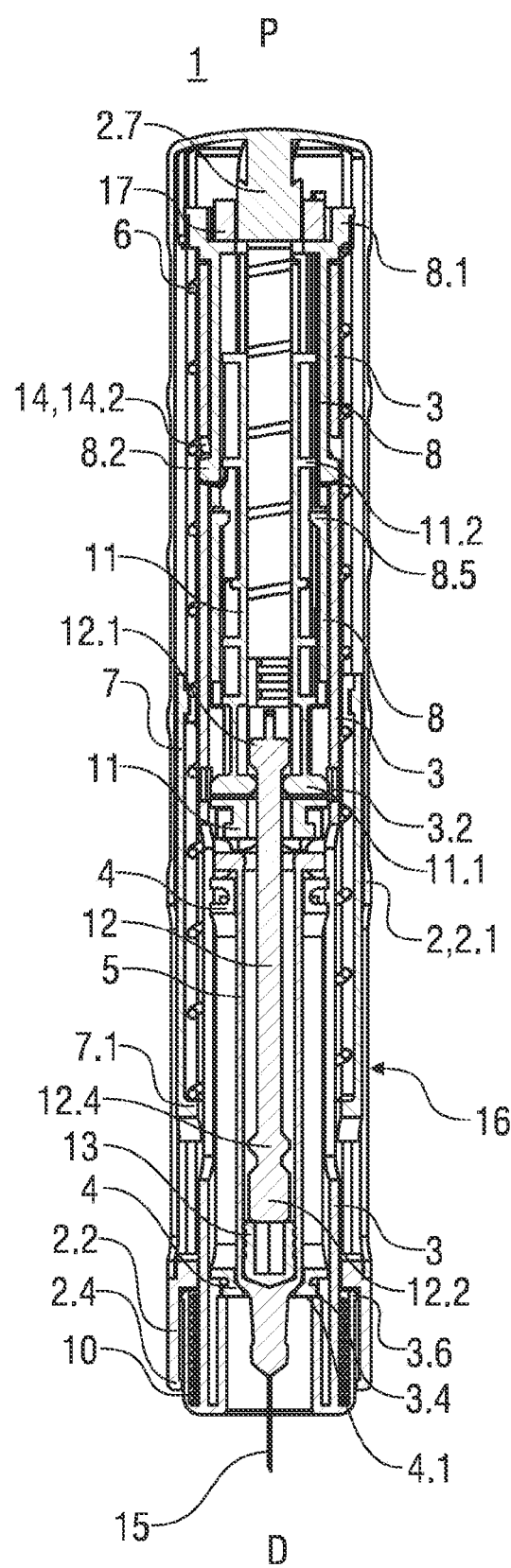

AUTOINJECTOR WITH AN INNER PLUNGER WHICH DISENGAGES THE OUTER PLUNGER TO RETRACT THE SYRINGE CARRIER

CROSS REFERENCE TO RELATED APPLICATIONS

The present application is a continuation of U.S. patent application Ser. No. 15/821,166, filed Nov. 22, 2017, which is a continuation of U.S. patent application Ser. No. 14/366,868, filed Jun. 19, 2014, now U.S. Pat. No. 9,827,381, which is a U.S. National Phase Application pursuant to 35 U.S.C. § 371 of International Application No. PCT/EP2012/076097, filed Dec. 19, 2012, which claims priority to European Patent Application No. 11194775.0, filed Dec. 21, 2011. The entire disclosure contents of these applications are herewith incorporated by reference into the present application.

TECHNICAL FIELD

The invention relates to an autoinjector for administering a medicament.

BACKGROUND

Administering an injection is a process which presents a number of risks and challenges for users and healthcare professionals, both mental and physical injection devices typically fall into two categories—manual devices and autoinjectors. In a conventional manual device, a user must provide force to drive a medicament through a needle. This is typically done by some form of button/plunger that has to be continuously pressed during the injection. There are numerous disadvantages for the user from this approach. For example, if the user stops pressing the button/plunger, the injection will stop and may not deliver an intended dose to a patient. Further, the force required to push the button/plunger may be too high for the user (e.g., if the user is elderly). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

There remains a need for an improved autoinjector.

SUMMARY

It is an object of the present invention to provide an improved autoinjector.

In an exemplary embodiment, an autoinjector according to the present invention comprises a case, a chassis slidably arranged in the case, a syringe carrier operably coupled to the chassis, an outer plunger selectively engaged to the chassis, an inner plunger selectively engaged to the outer plunger, and a drive spring applying a biasing force to the outer plunger. The biasing force is applied to the inner plunger when the inner plunger is engaged to the outer plunger. Rotation of the chassis causes the inner plunger to rotate relative to the outer plunger and disengage the outer plunger to remove the biasing force from the drive spring on the inner plunger. When the inner plunger disengages the outer plunger, the biasing force of the drive spring pushes the chassis to retract the syringe carrier relative to the case.

In an exemplary embodiment, the autoinjector further comprises a needle shroud slidably arranged in the case. Axial movement of the needle shroud relative to the case causes rotation of the chassis relative to the needle shroud.

In an exemplary embodiment, the autoinjector further comprises a firing nut rotatably disposed on the chassis. The firing nut engages the outer plunger when in a first angular position and disengages the outer plunger when in a second angular position. The case includes a stem adapted to rotate the firing nut from the first angular position to the second angular position. When the firing nut is in the second angular position, the biasing force of the drive spring pushes the outer plunger in a distal direction (D) relative to the case.

In an exemplary embodiment, the needle shroud includes a guide track adapted to engage a pin on the chassis. The pin moves from an angled portion to an axial portion of the guide track causing rotation of the chassis relative to the needle shroud when the needle shroud translates relative to the case.

In an exemplary embodiment, the autoinjector further comprises a coupling carrier coupled to the syringe carrier and selectively engaged to the inner plunger. The coupling carrier includes resilient arms adapted to releasably engage the inner plunger, and the biasing force of the drive spring causes the inner plunger to deflect the resilient arms when a front stop on the syringe carrier abuts a shroud shoulder on the needle shroud. When the resilient arms disengage the inner plunger, the inner plunger is adapted to push a stopper in a syringe. The chassis includes a resilient clip adapted to engage a stop on the coupling carrier. When the biasing force of the drive spring pushes the chassis, the clip engages the stop and retracts the coupling carrier and the syringe carrier relative to the case.

In an exemplary embodiment, the autoinjector further comprises a control spring axially biasing the needle shroud relative to the case.

In an exemplary embodiment, rotation of the chassis relative to the needle shroud causes rotation of the firing nut to a third angular position in which the firing nut is adapted to advance over the stem.

In an exemplary embodiment, the needle shroud includes a resilient non-return clip adapted to engage the case and prevent translation of the needle shroud relative to the case.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIGS. 1A and 1B show two longitudinal sections of an exemplary embodiment of an autoinjector in an initial state according to the present invention, FIGS. 6A and 6B show two longitudinal sections of an exemplary embodiment of an autoinjector with an injection needle extended beyond the distal end according to the present invention, FIGS. 8A and 8B show two longitudinal sections of an exemplary embodiment of an autoinjector after an injection according to the present invention.

Corresponding parts are marked with the same reference symbols in all figures.

DETAILED DESCRIPTION

Figure 2:
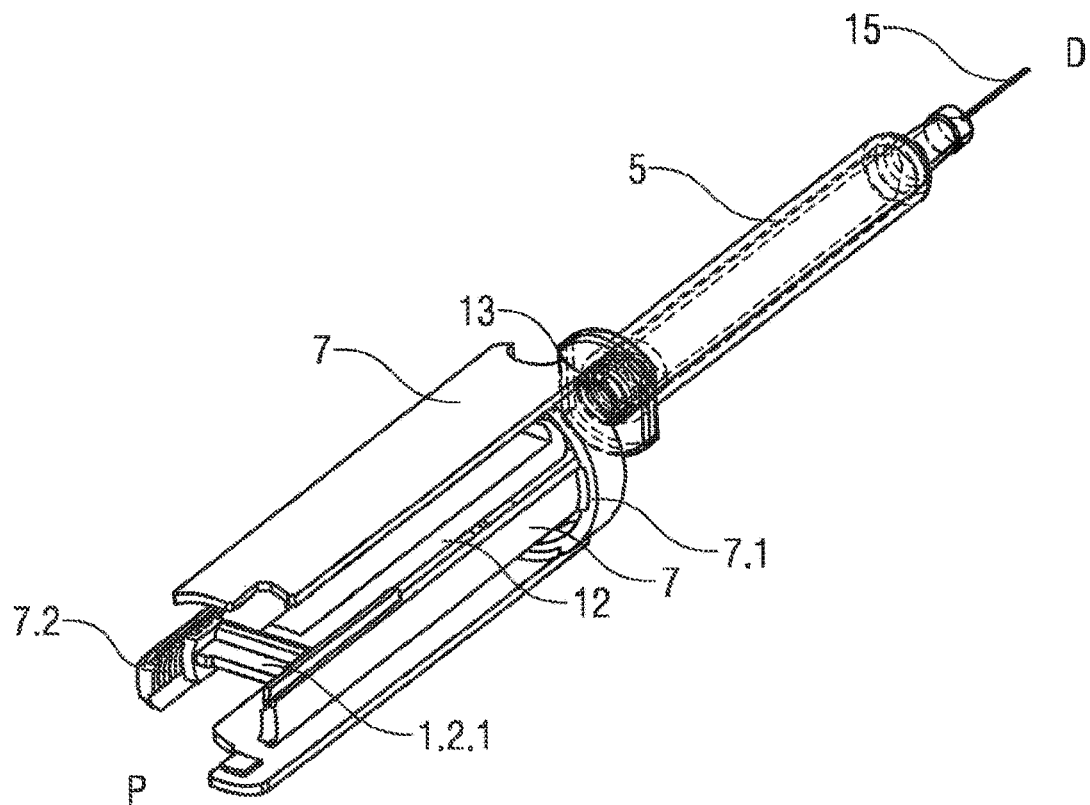
FIG. 2 is a perspective view of exemplary embodiments of a syringe, an inner plunger and an outer plunger for an autoinjector according to the present invention.

FIGS. 1A and 1B show two longitudinal sections of an exemplary embodiment of an autoinjector 1 for delivering a medicament. The sectional planes of the longitudinal sections are essentially oriented perpendicularly with respect to each other.

In an exemplary embodiment, the autoinjector 1 comprises an elongate case 2 comprising a rear case 2.1 coupled to a front case 2.2. A needle shroud 3 is telescopically arranged on the case 2 and may be resiliently coupled to the front case 2.2 by a control spring 10 which applies a biasing force on the needle shroud 3 toward a distal direction D.

A syringe carrier 4 is slidably disposed in the case 2 and is arranged to hold a syringe 5 having a needle 15. As explained further below, the syringe carrier 4 includes an abutment surface 4.1 formed on its distal end that is adapted to abut a shoulder 3.4 formed on the distal portion of the needle shroud 3 when the syringe carrier 4 is moving axially in the distal direction D relative to the needle shroud 3. A distance between a distal face of the needle shroud 3 and the shoulder 3.4 may define the injection depth of the needle 15.

A proximal end of the needle shroud 3 is adapted to abut a chassis 8 which is slidably disposed in the case 2. A collar 8.1 disposed on a proximal end of the chassis 8 acts as a proximal bearing for a drive spring 6, which bears distally on a shoulder 7.1 on an outer plunger 7 that is telescopically arranged on the chassis 8.

Figure 7:
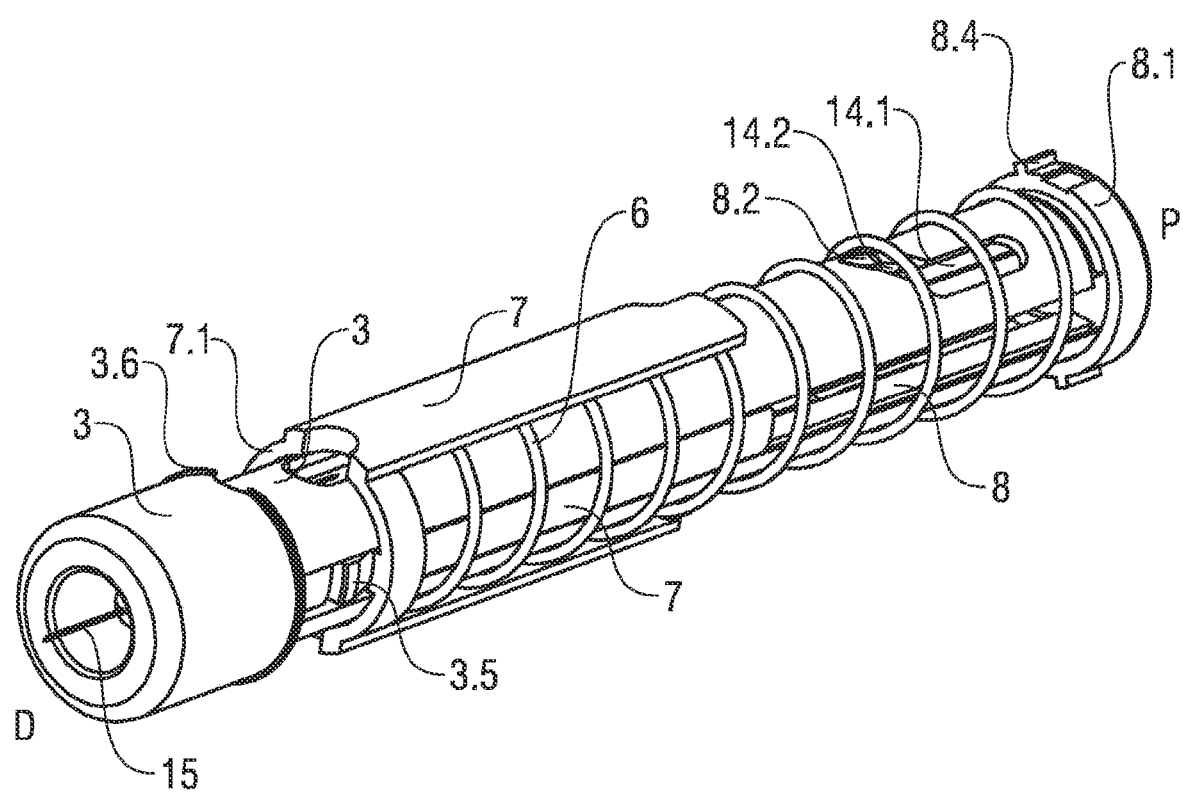
FIG. 7 is a perspective view of exemplary embodiments of internal components of an exemplary embodiment of an autoinjector with a needle extended according to the present invention.

As shown in FIG. 7, in an exemplary embodiment, the collar 8.1 includes a radial protrusion 8.4 which is adapted to prevent rotation of the chassis 8 relative to the rear case 2.1 when the autoinjector 1 is pressed against an injection site. In an exemplary embodiment, the radial protrusion 8.4 is adapted to engage a channel formed in the rear case 2.1, and when the needle shroud 3 is pressed against the injection site, the radial protrusion 8.4 abuts the channel and is prevented from rotating relative to the rear case 2.1. Prior to and after use, the radial protrusion 8.4 does not abut the channel and thus the collar 8.1 (and chassis 8) may rotate relative to the rear case 2.1.

Referring back to FIGS. 1A and 1B, in an exemplary embodiment, a firing nut 17 is selectively engaged to outer plunger 7. The firing nut 17 may rotatably sit in a cavity of the collar 8.1. The firing nut 17 may include teeth 17.1 which are adapted to engage teeth 7.2 formed on a surface of the outer plunger 7. The teeth 17.1 on the firing nut 17 may be formed on a selected portion of the firing nut 17, such that rotation of the firing nut 17 relative to the outer plunger 7 from a first angular position to a second angular position may disengage the outer plunger from the firing nut 17.

The teeth 7.2 of the outer plunger 7 may also engage corresponding teeth 12.1 formed on an inner plunger 12. For example, the inner plunger 12 may include a stem and a transverse element coupled to a proximal portion of the stem, and an outer surface of the transverse element may include the teeth 12.1 for engaging the teeth 7.2 on the outer plunger 7.

Figure 3:
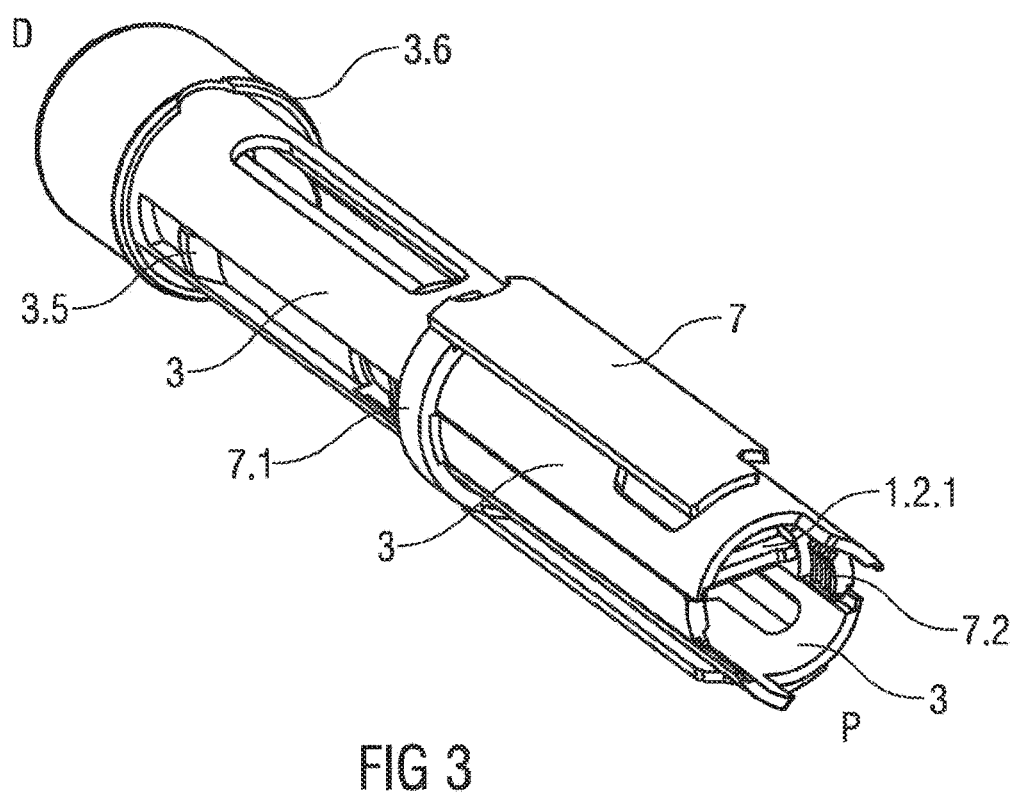
FIG. 3 is a perspective view of an exemplary embodiment of an outer plunger guided in a needle shroud according to the present invention.

As shown in FIG. 3, the outer plunger 7 may be keyed to the needle shroud 3 to allow axial relative movement but prevent rotational relative movement. For example, the outer plunger 7 may include a plurality of legs, and one or more of the legs may be adapted to engage a groove or channel formed in the needle shroud 3.

Referring back to FIGS. 1A and 1B, a coupling carrier 11 is slidably arranged in and keyed to the chassis 8 (allowing for relative translation and joint rotation) and is coupled to the syringe carrier 4. The inner plunger 12 is arranged telescopically in the coupling carrier 11 to allow for axial movement of the inner plunger 12 relative to the coupling carrier 11 and joint rotation with the coupling carrier 11 relative to the chassis 8. Two resilient arms 11.1 on the coupling carrier 11 are arranged to selectively engage a groove between a first plunger shoulder 12.2 and a second plunger shoulder 12.4 on the inner plunger 12 in a manner to couple the inner plunger 12 and the coupling carrier 11 for joint axial translation. In an exemplary embodiment, the resilient arms 11.1 and the first plunger shoulder 12.2 are in a ramped engagement so as to allow the resilient arms 11.1 to deflect radially and disengage the inner plunger 12.

In an exemplary embodiment, the resilient arms 11.1 are maintained in engagement with the first plunger shoulder 12.2, because the needle shroud 3 abuts the resilient arms 11.1. However, the needle shroud 3 includes first apertures 3.2 which, when aligned with the resilient arms 11.1, allow space for the resilient arms 11.1 to deflect radially and disengage the inner plunger 12.

In an exemplary embodiment, a proximal end of the case 2 includes a stem 2.7 extending in the proximal direction and having a thread adapted to engage a corresponding thread 17.2 formed in the firing nut 17. As explained further below, when the thread on the stem 2.7 engages the thread 17.2 on the firing nut 17, the firing nut 17 rotates relative to the outer plunger 7.

In an exemplary embodiment, a cap (not shown) is removably coupled to the front case 2.2 and/or the needle shroud 3. The cap may be coupled to a needle sheath (not illustrated) arranged on the needle 15, and removal of the cap may remove the needle sheath.

FIGS. 1A and 1B show the autoinjector 1 in an initial state, prior to use. Prior to use, the needle shroud 3 extends from the case 2 under the biasing force of the control spring 10 to cover a distal tip of the needle 15. As shown in FIG. 7, in an exemplary embodiment, the needle shroud 3 includes a guide track 14 having an axial portion 14.1 and an angled portion 14.2, and a pin 8.2 on the chassis 8 engages the guide track 14. In the initial state, the pin 8.2 is in a distal portion of the angled section 14.2. Referring back to FIGS. 1A and 1B, the firing nut 17 and the inner plunger 12 are both engaged to the outer plunger 7, and the coupling carrier 11 is engaged to the inner plunger 12.

Figure 4A:
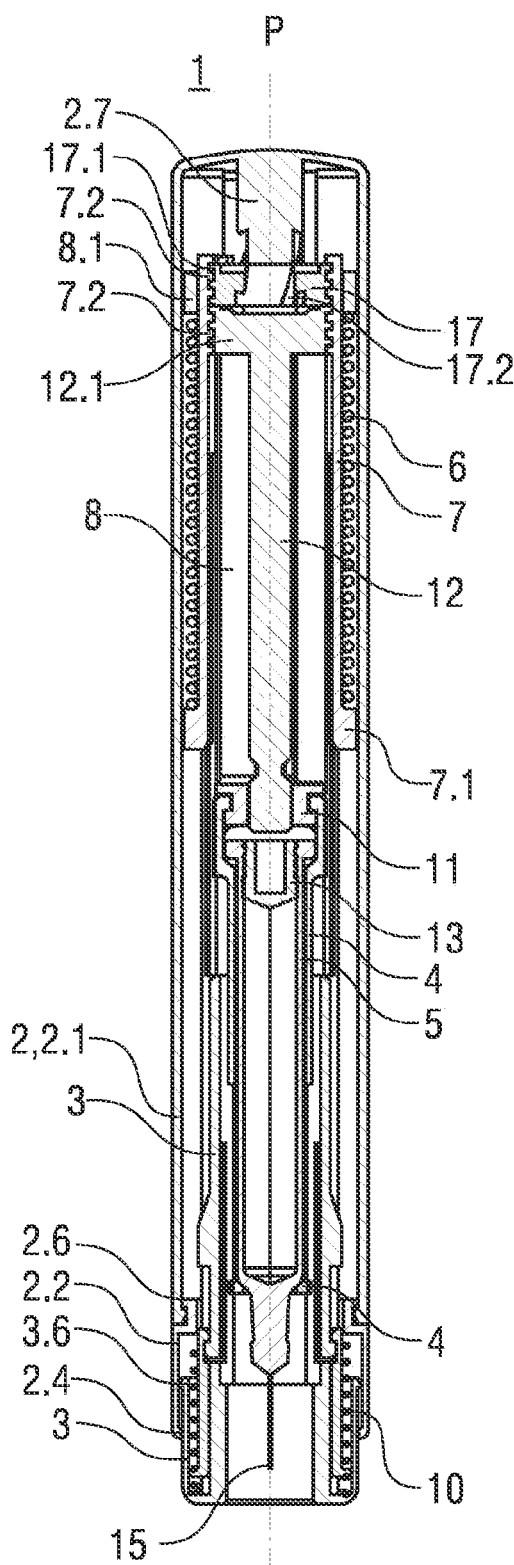
FIGS. 4A and 4B show two longitudinal sections of an exemplary embodiment of an autoinjector with a distal end pushed against an injection site according to the present invention.
Figure 4B:
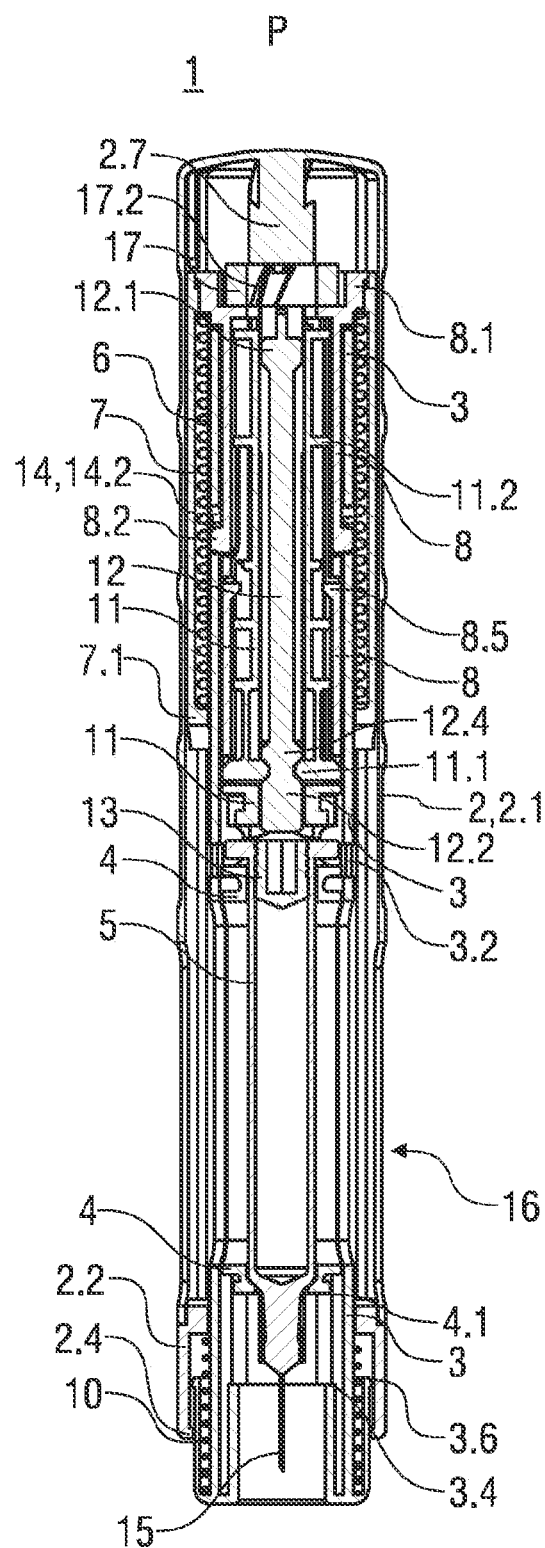

As shown in FIGS. 4A and 4B, when the autoinjector 1 is pressed against an injection site, the needle shroud 3 translates into the case 2 in the proximal direction P, compressing the control spring 10. The needle shroud 3 pushes the chassis 8 in the proximal direction P. Movement of the chassis 8 results in corresponding movement of the firing nut 17 which also results in corresponding movement of the outer plunger 7, since the firing nut 17 is engaged to the outer plunger 7 via teeth 17.1. Since the inner plunger 12 is engaged to the outer plunger 7, the inner plunger 12 and the coupling carrier 11, the syringe carrier 4 and the syringe 5 move in conjunction with the inner plunger 12.

Figure 5A:
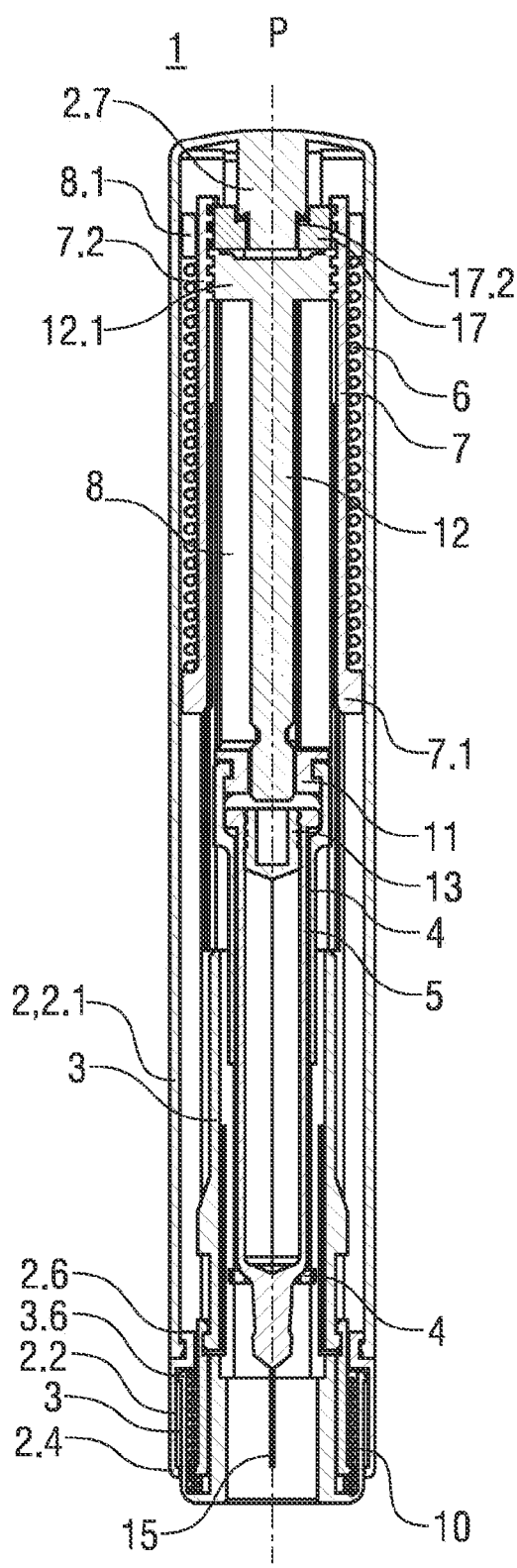
FIGS. 5A and 5B show two longitudinal sections of an exemplary embodiment of an autoinjector with a distal end pushed against an injection site according to the present invention.
Figure 5B:
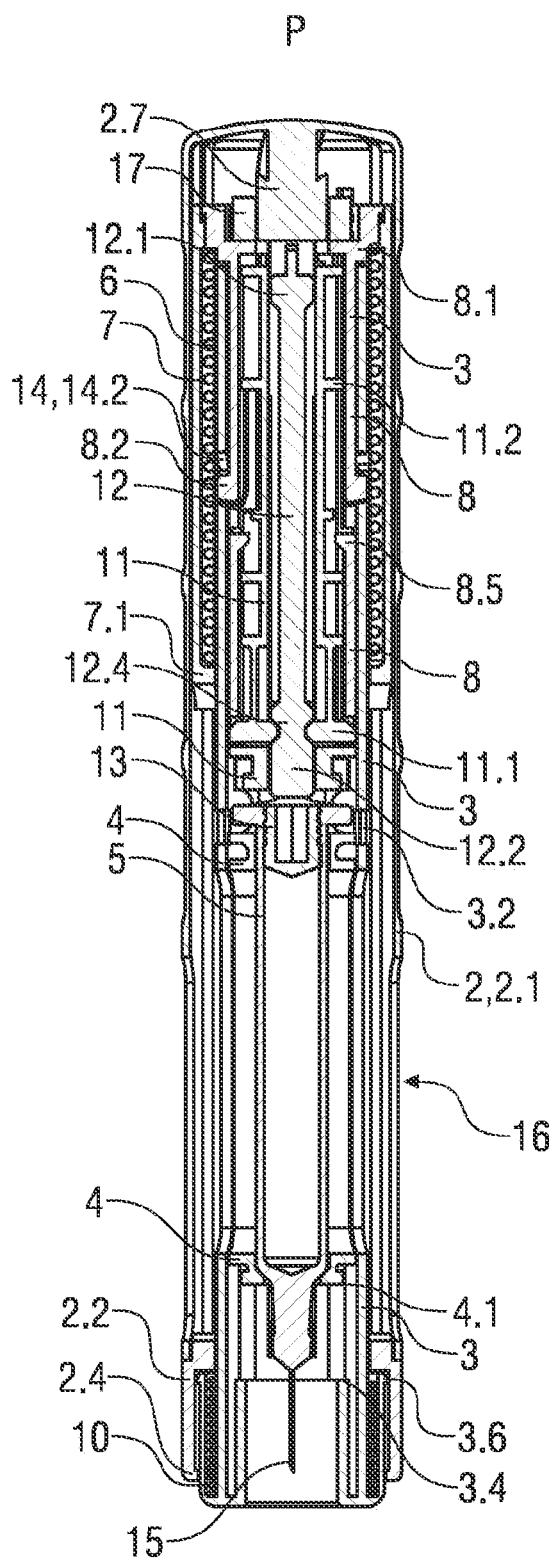

As shown in FIGS. 5A and 5B, the autoinjector 1 is pressed further against the injection site (substantially fully compressing the control spring 10), and the stem 2.7 engages the firing nut 17. As the stem 2.7 engages the firing nut 17, the firing nut 17 rotates from the first angular position to the second angular position, disengaging the outer plunger 7.

As shown in FIGS. 6A and 6B, when the firing nut 17 rotates into the second angular position, the outer plunger 7 is released from the chassis 8, and the drive spring 6 pushes the outer plunger 7 in the distal direction D. Because the inner plunger 12 is coupled to the outer plunger 7, the inner plunger 12 (and the coupling carrier 11, syringe carrier 4 and syringe 5) moves in the distal direction D. Movement of the syringe carrier 4 in the distal direction D leads to insertion of the needle 15 in the injection site. A penetration depth of the needle 15 is defined by a front stop 4.1 on the syringe carrier 4 abutting an inner distal shroud shoulder 3.4 on the needle shroud 3.

As shown in FIGS. 8A and 8B, when the front stop 4.1 on the syringe carrier 4 abuts the inner distal shroud shoulder 3.4 on the needle shroud 3, the resilient arms 11.1 of the coupling carrier 11 align with the first apertures 3.2 of the needle shroud 3, and the force of the drive spring 6 causes the first plunger shoulder 12.2 to deflect the resilient arms 11.1 of the coupling carrier 11 into the first apertures 3.2. When the resilient arms 11.1 are deflected, the inner plunger 12 moves in the distal direction D relative to the coupling carrier 11. The inner plunger 12 abuts a stopper 13 in the syringe 5 and pushes the stopper 13 in the distal direction D to expel the medicament from the needle 15.

Figure 9A:
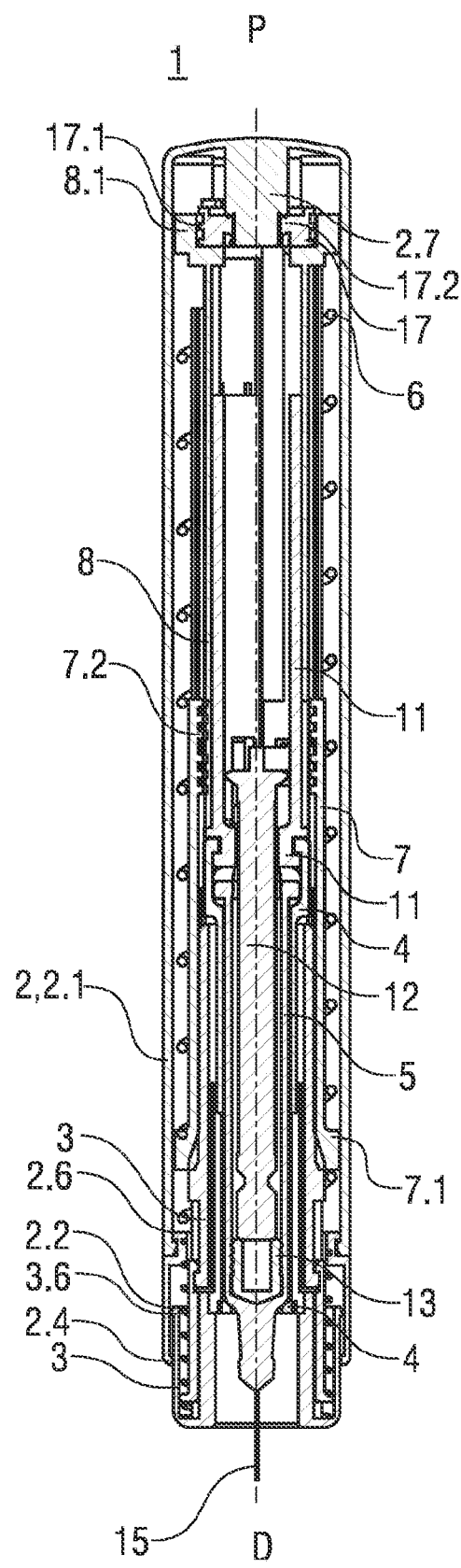
FIGS. 9A and 9B show two longitudinal sections of an exemplary embodiment of an autoinjector removed from an injection site according to the present invention.
Figure 9B:
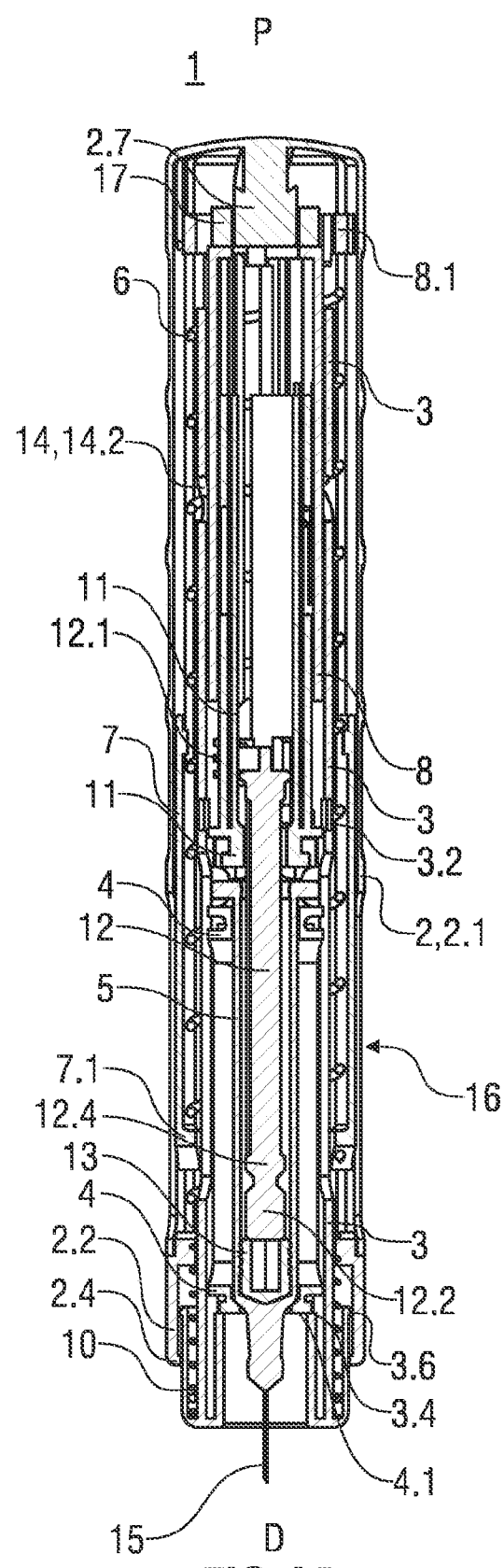

As shown in FIGS. 9A and 9B, when the autoinjector 1 is removed from the injection site after an injection is complete or during the injection, the biasing force of the control spring 10 causes the needle shroud 3 to translate in the distal direction D relative to the case 2. Under the force of the drive spring 6, the outer plunger 7 translates in the distal direction D relative to the case 2. As the needle shroud 3 translates in the distal direction D relative to the case 2, the engagement of the pin 8.2 on the chassis 8 and the guide track 14 causes the chassis 8 to rotate relative to the case 2. As the needle shroud 3 translates, the geometry of the guide track 14 causes the pin 8.2 to move through the angled portion 14.2 of the guide track 14 causing rotation of the chassis 8 relative to the needle shroud 3 and into the axial portion 14.1 of the guide track 14 which allows for axial movement of the needle shroud 3 relative to the chassis 8. Because the outer plunger 7 is keyed to the needle shroud 3, the chassis 8 rotates relative to the outer plunger 7 and causes rotation of the coupling carrier 11 which, in turn, rotates the inner plunger 12 to disengage from the outer plunger 7. Thus, the teeth 12.1 on the inner plunger 12 disengage the teeth 7.2 on the outer plunger 7. Further, extension of the needle shroud 3 relative to the case 2 is limited by the pin 8.2 abutting the proximal end of the axial portion 14.1 of the guide track 14 during translation of the needle shroud 3.

When the inner plunger 12 disengages the outer plunger 7, the force of the drive spring 6 does not act on the inner plunger 12. Thus, even if the autoinjector 1 is removed from the injection site during the injection, the expulsion of the medicament from the syringe 5 will stop, because there is no force to move the inner plunger 12 (and the stopper 13).

As the insertion depth of the needle 15 is defined by the syringe carrier 4 contacting the needle shroud 3, allowing the needle shroud 3 to re-advance on removal from the injection site could also allow the syringe 5 to advance further. In order to avoid this, one or more resilient clips 8.5 are arranged on the chassis 8 to engage a stop 11.2 on the coupling carrier 11 at the end of the rotation of the chassis 8. The clips 8.5 prevents the coupling carrier 11 (and the syringe carrier 4 coupled thereto and the syringe 5) from advancing in the distal direction D after the autoinjector 1 has been removed from the injection site.

Figure 10A:
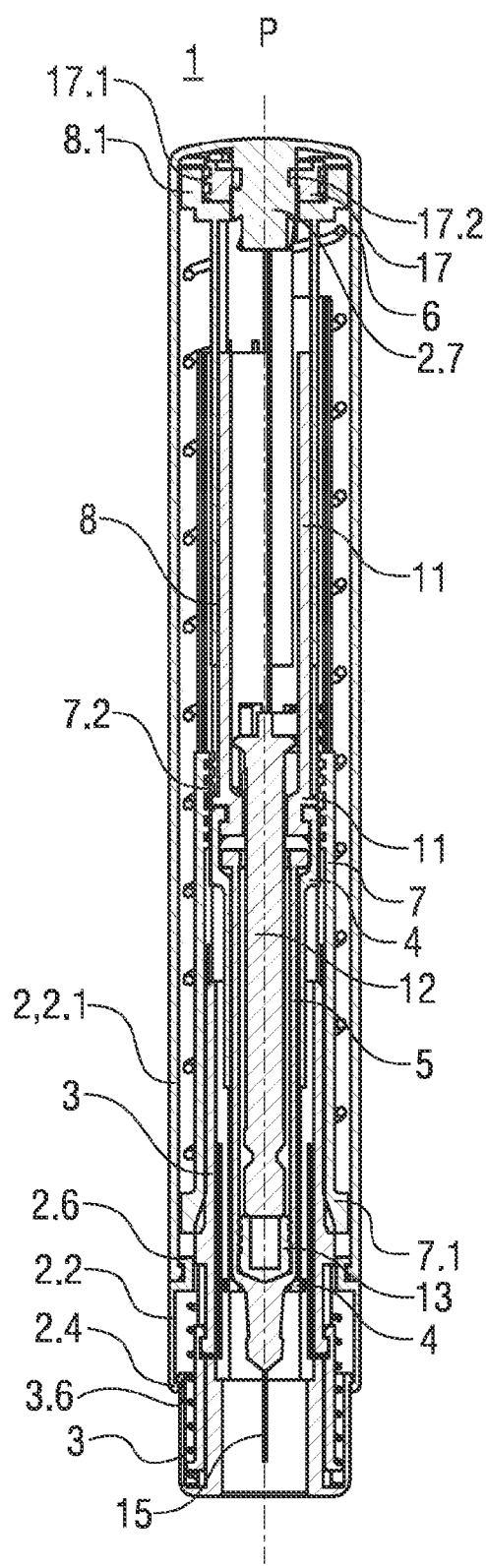
FIGS. 10A and 10B show two longitudinal sections of an exemplary embodiment of an autoinjector removed from an injection site according to the present invention.
Figure 10B:
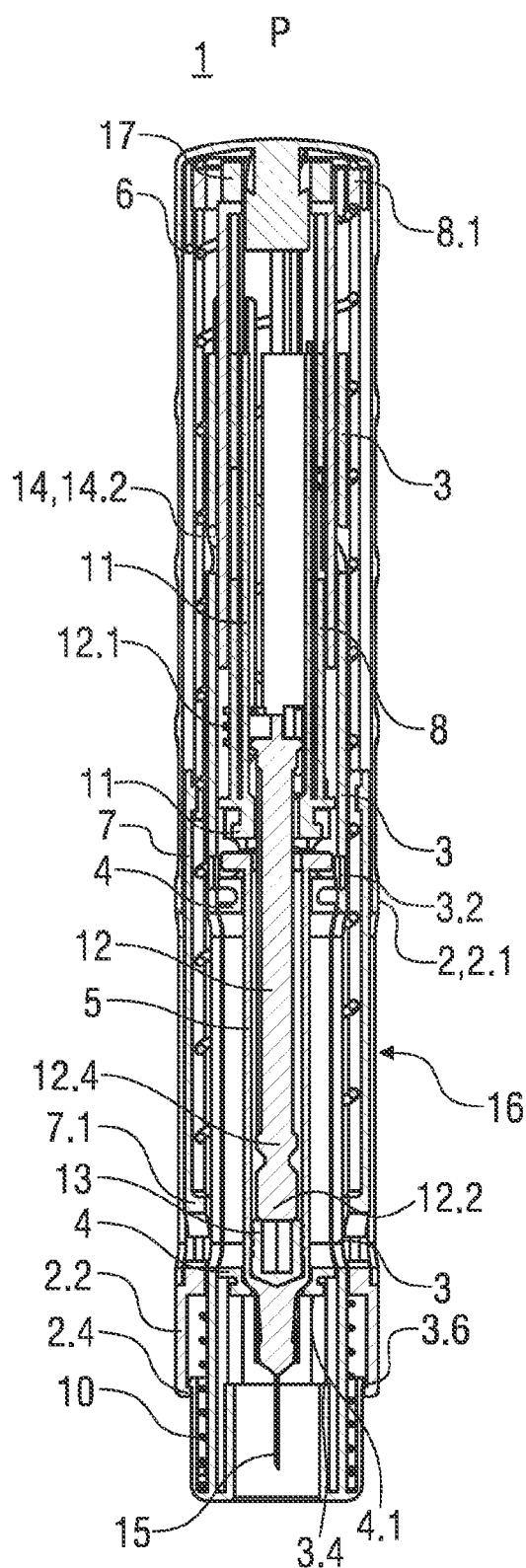

FIGS. 10A and 10B show the needle shroud 3 in its extended state and the syringe carrier 4 (and the syringe 5) in a retracted state. In an exemplary embodiment, when the chassis 8 rotates by movement of the guide pin 8.2 in the guide track 14, the firing nut 17 rotates to a third angular position and disengages the thread on the stem 2.7 (which was preventing movement of the firing nut 17 in the proximal direction P relative to the stem 2.7), allowing the firing nut 17 and the collar 8.1 to be pushed in the proximal direction P against the proximal end of the case 2 under the force of the drive spring 6. In another exemplary embodiment, the force of the drive spring 6 pushes the collar 8.1 in the proximal direction P causing the firing nut 17 to rotate to the third angular position and disengages the thread on the stem 2.7 (or, alternatively, follows the thread on the stem 2.7 until it abuts the proximal end of the case). The proximal movement of the collar 8.1 causes a proximal movement of the chassis 8, the coupling carrier 11 and the syringe carrier 4, which retracts the syringe 5 and the needle 15 in the proximal direction P relative to the case 2. For example, the stop 11.2 on the coupling carrier 11 may engage the clip 8.5 on the chassis 8, such that the proximal movement of the chassis 8 may result in a corresponding proximal movement of the coupling carrier 11. The residual force in the drive spring 6 may maintain the syringe 5 in a retracted position relative to the case 5.

Hooks 3.6 on a distal end of the needle shroud 3 may engage a distal case shoulder 2.4 to limit extension of the needle shroud 3 relative to the case 2 under the force of the control spring 10.

In an exemplary embodiment, a resilient non-return clip (not shown) may be arranged on the needle shroud 3 and adapted to engage the case 2 after the needle shroud 3 has been extended. The non-return clip may prevent the needle shroud 3 from moving in the proximal direction P relative to the case 2 if the autoinjector 1 is pressed against a subsequent injection site or during handling after an injection.

In an exemplary embodiment, a viewing window 16 is arranged in the case 2 for inspecting contents of the syringe 5.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:
1. An autoinjector comprising:
   a case comprising a rear case;
   a needle shroud slidably arranged in the case;
   a plunger arranged within the case and configured to be released in a distal direction from the rear case by a rotation caused by a translation of the needle shroud in a proximal direction relative to the case, the plunger configured to push a stopper in a syringe containing a medicament when the plunger moves in the distal direction; and a drive spring configured to apply a biasing force to the plunger for injection of the medicament from the syringe, wherein the autoinjector is configured such that axial movement of the needle shroud relative to the case causes rotation of the plunger relative to the case.

2. The autoinjector according to claim 1, further comprising a control spring that is configured to be compressed by the needle shroud when the needle shroud moves in the proximal direction.

3. The autoinjector according to claim 2, further comprising hooks on a distal end of the needle shroud and a distal case shoulder on the case.

4. The autoinjector according to claim 3, wherein the hooks are adapted to engage the distal case shoulder to limit extension of the needle shroud relative to the case under a force of the control spring.

5. The autoinjector according to claim 4, wherein the hooks extend radially outwards relative to a longitudinal axis of the autoinjector.

6. The autoinjector according to claim 5, further comprising resilient non-return features that are arranged on the needle shroud and that are adapted to engage the case after the needle shroud has been extended after an injection.

7. The autoinjector according to claim 1, further comprising a syringe carrier adapted to hold the syringe.

8. The autoinjector according to claim 7, further comprising the syringe.

9. The autoinjector according to claim 8, wherein the syringe comprises a needle.

10. The autoinjector according to claim 1, wherein the rotation is a relative rotation between the plunger and the rear case.

11. The autoinjector according to claim 1, wherein the plunger is rotationally coupled to the needle shroud.

12. The autoinjector according to claim 1, wherein the autoinjector is configured to inject the medicament upon release of the plunger from the rear case.

13. A method for delivering a medicament from an autoinjector into a subject, the method comprising:

axially moving a needle shroud of the autoinjector relative to a case of the autoinjector causing a rotation of a plunger of the autoinjector relative to the case; and delivering the medicament from the autoinjector into the subject by releasing the plunger from a rear case of the case by a rotation caused by a translation of the needle shroud in a proximal direction relative to the case, pushing a stopper of a syringe of the autoinjector in a distal direction relative to the rear case by a biasing force of a drive spring to deliver the medicament from the syringe.

14. The method according to claim 13, further comprising engaging a resilient member of the needle shroud to the case after delivering the medicament to limit proximal movement of the needle shroud relative to the case.

15. The method according to claim 13, wherein the medicament comprises a pharmaceutically active compound.

16. The autoinjector according to claim 1, comprising a firing nut rotationally coupled to the plunger, wherein the rotation caused by the translation of the needle shroud in the proximal direction relative to the case is a rotation of the firing nut.

17. The autoinjector according to claim 1, wherein the needle shroud comprises a resilient member configured to engage the case after the injection of the medicament from the syringe to limit proximal movement of the needle shroud relative to the case.

18. The autoinjector according to claim 1, further comprising an angled protrusion on a distal portion of the needle shroud, the angled protrusion being angled relative to a longitudinal axis of the case.

19. The autoinjector according to claim 18, wherein the angled protrusion is configured to engage the case to limit distal movement of the needle shroud.

20. An autoinjector comprising:

a case comprising a rear case;

a needle shroud slidably arranged in the case between a retracted position and an extended position;

a plunger arranged within the case and configured to be released in a distal direction from the rear case by a rotation caused by a translation of the needle shroud in a proximal direction relative to the case, the plunger configured to push a stopper in a syringe containing a medicament when the plunger moves in the distal direction; and a drive spring configured to apply a biasing force to the plunger for injection of the medicament from the syringe, wherein the needle shroud comprises a resilient member configured to engage the case after the injection of the medicament from the syringe to limit proximal movement of the needle shroud relative to the case toward the retracted position.

21. The autoinjector according to claim 20, wherein the resilient member is configured to engage the case after needle shroud has been in the extended position.

22. The autoinjector according to claim 20, wherein the resilient member is a non-return feature.

23. The autoinjector according to claim 20, wherein the autoinjector is configured such that axial movement of the needle shroud relative to the case causes rotation of the plunger relative to the case.

* * * * *